United States Patent [19]

Morgenstern

[11] Patent Number: 4,644,956
[45] Date of Patent: Feb. 24, 1987

[54] PHYSIOLOGICAL TEST PROBE

[76] Inventor: Jurgen Morgenstern, Im Heidewinkel 33, 4000 Dusseldorf, Fed. Rep. of Germany

[21] Appl. No.: 661,236

[22] Filed: Oct. 15, 1984

[30] Foreign Application Priority Data

Oct. 13, 1983 [DE] Fed. Rep. of Germany ....... 3337188
Sep. 21, 1984 [DE] Fed. Rep. of Germany ....... 3434657

[51] Int. Cl.$^4$ ............................................. A61B 5/04
[52] U.S. Cl. .................................... 128/642; 128/698; 128/715; 128/736
[58] Field of Search ............... 128/642, 639, 698, 715, 128/736, 775, 778, 785

[56] References Cited

U.S. PATENT DOCUMENTS

| | | | |
|---|---|---|---|
| 2,611,368 | 9/1952 | Pecora | 128/639 |
| 3,750,650 | 8/1973 | Ruttgers | 128/642 |
| 3,999,555 | 12/1976 | Person | 128/785 |
| 4,011,875 | 3/1977 | Lehr et al. | 128/785 |
| 4,177,818 | 12/1979 | DePedro | 128/785 |
| 4,254,764 | 3/1981 | Neward | 128/642 |
| 4,680,961 | 3/1978 | Eaton | 128/642 |

FOREIGN PATENT DOCUMENTS 2247263 5/1975 France .................................. 128/785

Primary Examiner—William E. Kamm
Attorney, Agent, or Firm—Holman & Stern

[57] ABSTRACT

A physiological test probe, in particular a vaginal electrode for the derivation of the foetal electrocardiogram, adapted to be transcervically fixed by means of points to the skin of the foetal head and attached to an output conductor cable. The probe may be a clip having a pair of planar parallel legs extending from a partially circular spring portion and having inwardly directed punctiform teeth on the free ends thereof, or may be provided with invasive contact points which are obliquely angled forwards from the longitudinal probe axis and ensure a good contact and as little damage as possible inflicted to the skin tissue of the foetal head. This probe is suitable for mounting elements associated with further measuring systems in order to allow remote instrumentally monitored observation of the birth process. The clip legs of one embodiment are mutually elastically connected and terminally provided with teeth so that on relaxation of the spring a skin fold is drawn into the gap between the clip legs and the skin fold is firmly held at a defined contact pressure.

7 Claims, 15 Drawing Figures

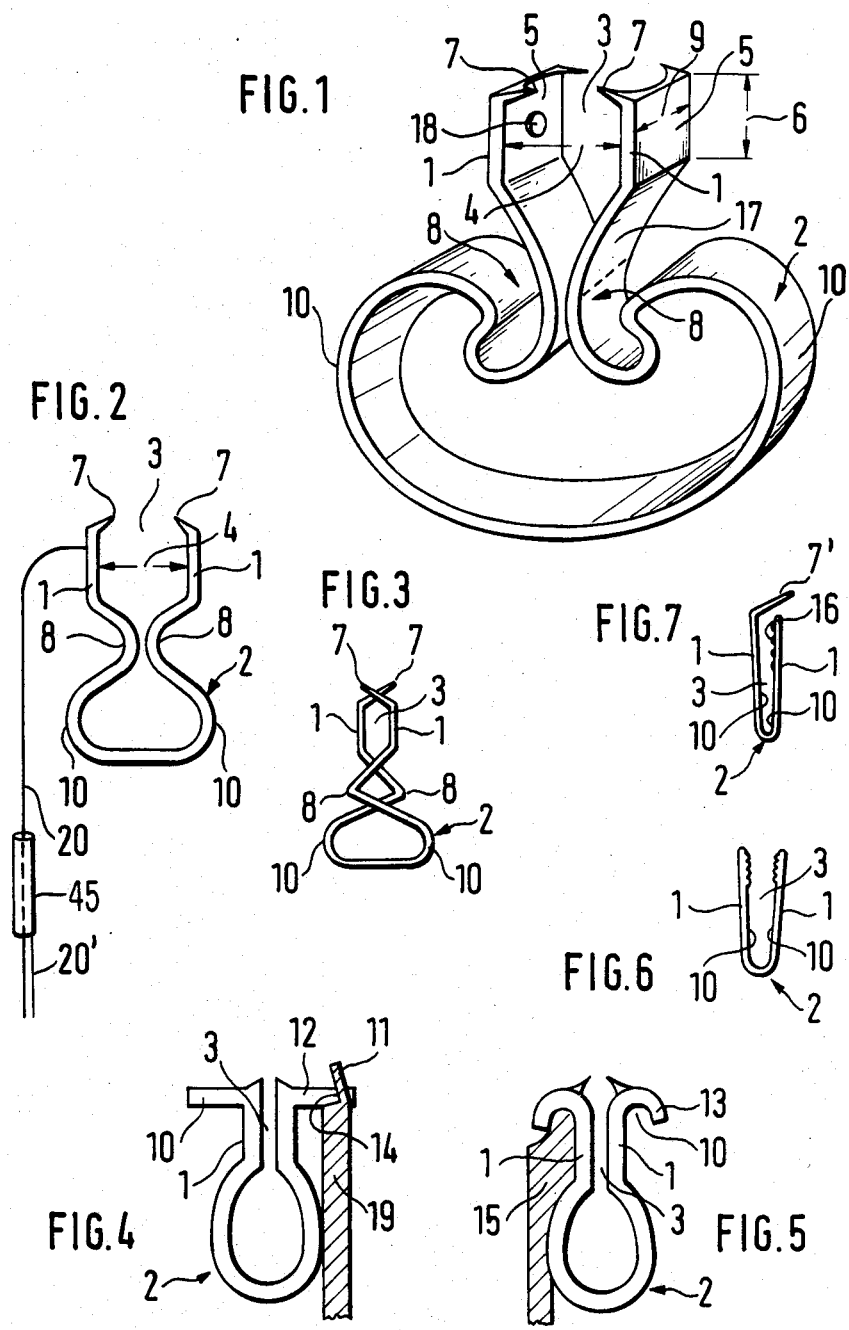

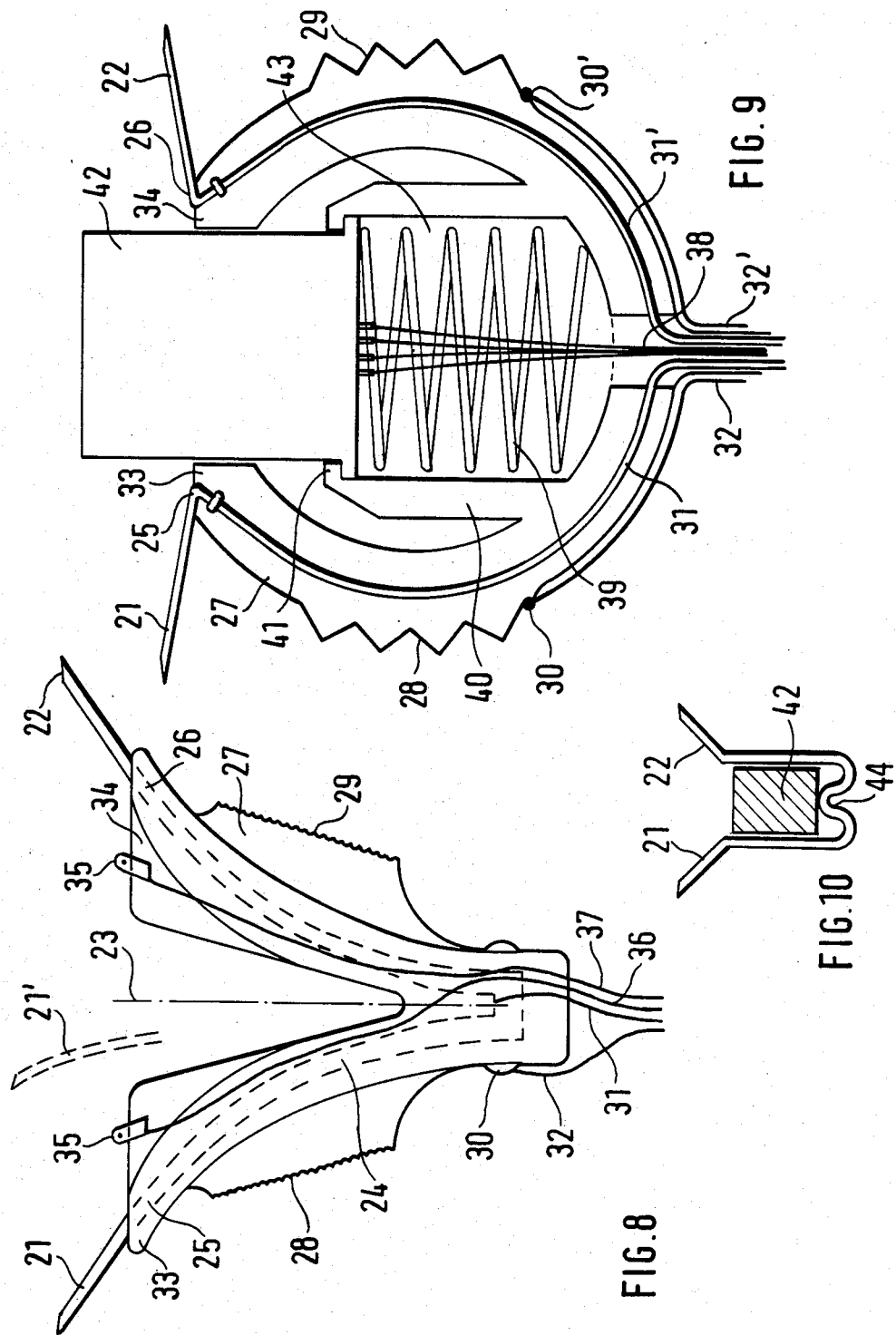

PHYSIOLOGICAL TEST PROBE

BACKGROUND OF THE INVENTION

1. Field of the Invention

The invention relates to a physiological test probe of the type which may be used to derive foetal electrocardiograms.

2. Description of the Prior Art

Test probes of this type are by their basic construction appropriate for picking up the foetal electrocardiogram throughout the whole of the birth process. According to Edward H. Hon, Amer. J. Obstet. Gynec. Vol. 86, 1963, page 773 a test probe of this kind is constructed as a vaginal electrode with contact points by modifying a suture clip and adapting it to be applied by means of forceps. In principle we are here dealing with a needle electrode. In other words, it presupposes a comparatively deep penetration of the point into the skin of the foetal head. Such a clip can be detached only with considerable difficulty prior to the actual birth of the child. Moreover, in view of the open-and shut-bending action it is not suitable for repeated use, as was found by H. W. Junge, 9, Geburtshilfe und Frauenheilkunde 29.2. page 133.

Also known, according to Edward H. Hon, Yale Journal of Biology and Medicine, Vol. 32, April, 1960, are resilient needle-shaped electrodes which partly slide past one another with their contact points and thereby are liable to damage tissues. The contact points penetrate into the head skin or scalp due to the closing of a clip and a derivation cable is attached to said clip. The counter electrode terminates exposed at a point which is insulated relative to said clip so that there is a contact with the mother. Also, according to Charles A. Hunter, Kenneth G. Lansford, Suzanne B. Knoebel and Robert J. Braunlin, Obstetrics and Gynecology, Vol. 16, 1960, page 567, the clip may be replaced by a spring. In that case the spring is slidably arranged in a guide tube from which project only the frontal sections with the angled contact points. However, in order to close the clip or to close the spring it is always necessary to apply additional forces which makes unnecessarily severe demands on the concentration of the attending doctor in actual birth conditions.

BRIEF SUMMARY OF THE INVENTION

By contrast it is the object of the present invention to develop a physiological test probe of the kind specified further in the sense that it affords a substantially improved contact-making on the one hand and, on the other hand that the skin tissues are treated delicately and carefully during probe application. Above all, the new test probe will also present the facility of applying further measuring or test elements which are to be applied to the application area of the head in order to allow the birth process being monitored not only electrocardiographically but also by other kinds of measurements.

Accordingly the invention is based on the principle of fixing to a predeterminable value the relative distance between the points in applied position by means of a spring which is brought into the relaxed or non-tensioned state thereof and of applying any further measuring element at a defined force to the skin area.

In a first basic embodiment of the invention the test probe establishes contact with the head skin by pressure application to the mutually opposite faces of the clip legs whilst the teeth at the ends of the clip legs merely serve to hold or retain the device. They do not have to penetrate into the skin of the head because the contact-making function does not depend on them. The gap of which height and breadth are defined by the clip legs has a predeterminable width so that optimum application pressure relative to the skin of the foetal head is assured. On application of the probe this skin is engaged by the teeth on the open clip legs; when the spring is released the legs close up and in so doing draw in between them a skin fold which is then exposed to the pressure of the sides of the clip legs. The large area of engagement or application on the clip legs offers excellent opportunities for associating the pick-ups of further measuring devices with the clip legs in order to apply further sensors to the skin of the foetal head. For example, one of the clip legs may accomodate a weak light source and the other a photodiode thus enabling blood circulation to be measured. The clip legs further allow the fitting thereon of electrodes to measure oxygen supply and of acceleration pick-ups to monitor the birth mechanics. In all such cases the precisely defined operative engagement of the clip leg side faces with the skin fold which has been drawn into the gap therebetween which is enabled by virtue of the test probe according to this invention constitutes a considerable advantage. Application of the probe may be done by means of forceps, the forceps engaging with the application faces of the spring and being introduced in tensed condition. On tension release and opening of the spring the forceps can be readily retracted. It is equally easy to remove the probe by means of forceps. However, it is also possible to make use of a slidable plunger or like conventional means for taking the spring from the tensed to the relaxed state thereof. To this end the spring is preferably arranged inside a sleeve or like part from which it may then be pushed out.

The circular ring-configuration of the spring is particularly useful and in that case the tension is in the annular or ring-part thereof whilst the clip legs are straight. With advantage arcuate junction zones may be provided between the legs and the spring which touch each other along a line extending in the direction of the breadth of the gap. In this fashion a turn-off point is created so that the clip legs open when the annular spring part is compressed. With the clip in this state the teeth are set down on the skin to be engaged thereby and then the spring may be released which results in the earlier described engagement of a skin fold between the clip legs. If the use of forceps is envisaged the force application faces of the spring will be suitably shaped for forceps engagement which may be positive, i.e. interfitting, or dynamic.

In one special embodiment of the invention the clip as such has the configuration of the Greek letter Omega in which case the force application faces would then be situated on the outwardly projecting feet of the clip limbs or legs. This means that such a spring would not be compressed but would be expanded for opening the clip legs. The feet of the clip legs may also be provided with engagement holes for the forceps tips. On the other hand the foot portions may also be bent back in the direction towards the legs of the clip so that in this event blunt, head-type forceps tips can be positively engaged between the clip legs and the bent-back foot portions thereof. Such a design is particularly good with a view to avoiding injuries.

Alternatively to the above described embodiment the clip may basically be of U-configuration to be expanded by means of the forceps tips. With this strongly simplified clip design the clip legs may, above all, be provided with teeth spaced over the inside of the legs; likewise it is possible for just one of the clip legs to have a terminal point whilst the opposite leg is provided with the said teeth spaced over the length thereof.

A special embodiment which safeguards against tilting or jamming of the spring resides in the provision between the spring and the clip legs of junction zones or regions which penetrate one another. To this end one of said junction zones has a slot and the other, opposite junction zone is reduced to the width of said slot whilst, moreover, both junction zones are curved oppositely to the spring in this region of mutual penetration. The elimination of the risk of tilting or wedging guarantees in this as in the other test probes according to the invention the precise juxtaposition of the critical measuring surfaces with the skin fold trapped therebetween.

In another basic embodiment of the invention the obliquely forwardly angled contact points penetrate into the headskin while the spring relaxes. In order to obtain this effect it is merely necessary to relieve the forceps-pressure faces which had previously been subject to the pressure applied by the tips of operating forceps. No further manual force need be applied to this type of probe. One special advantage of this arrangement resides in that the probe is inserted with closed forceps tips so that it has minimum extension and can be applied with a slightly opened os uteri.

Conveniently the contact points are directed outwards with an expansion capability of about 10 mm at the tips on spring relaxation whilst their length is less than 3 mm. If an expanding spring is used the force in that spring is preferably limited in such a way that it will tend to close up when a moderate longitudinal pull is applied to the probe and allow the latter to be extracted, for example in order to proceed to deliver the baby by caesarian section.

For the purpose of insulation the spring inclusive of a portion of the angled contact points provided thereon is provided with a closely adapted insulating cover or envelope of plastics material. This not only affords insulation but can also be conveniently provided on the external side with forceps-application faces to transmit forceps pressure to the spring. Furthermore, the said plastic covering or sheath, encasing also the angled portions of the probe may also be used to work as a depth stop to limit the depth of penetration of the contact points. The relative spacing of the contact points as well as their depth of penetration can thus be precisely pre-determined.

A first conductor cable for derivation of the foetal electrocardiogram issues from the contact points whilst a second conductor cable for derivation of the reference potential issues from a blunt mother-contact provided near the tip of the plastic sheath. Both these cables may also be introduced jointly with further cables leading for example to measuring elements such as thermo-variable resistors provided on that side of the sheath portion which comes into contact with the skin. Furthermore it is also possible to construct at least one of the contact points in the form of a hollow injector needle attached to a tube which may be routed jointly with the conductor cables.

The invention will now be described in detail with reference to the accompanying drawings showing embodiments thereof and wherein:

FIG. 1 is a perspective view of a first embodiment of the invention;

FIG. 2 is a schematic side elevational view of another embodiment;

FIG. 3 is a view similar to FIG. 2 of a further embodiment

FIG. 4 and

Figure 11:
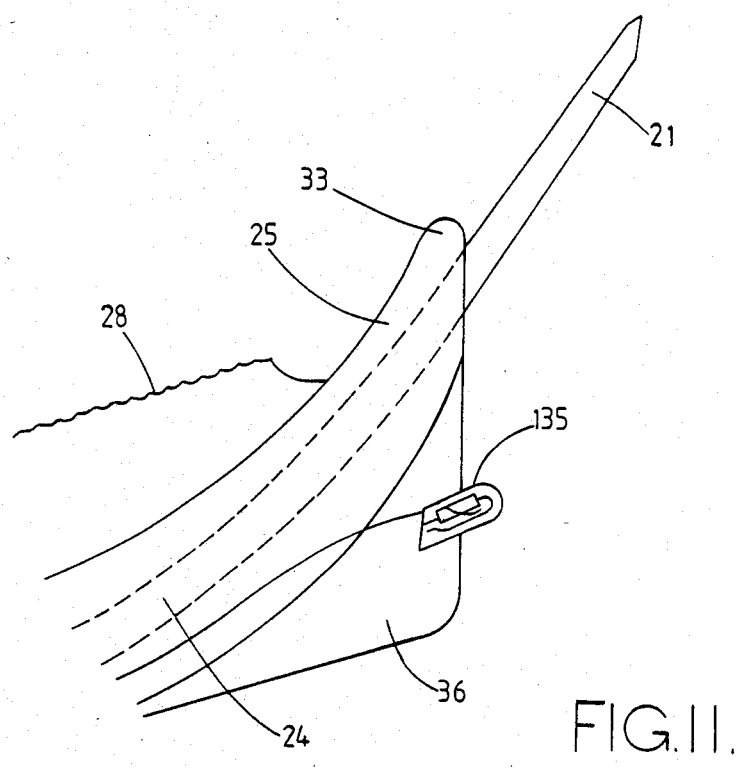
Figure 12:
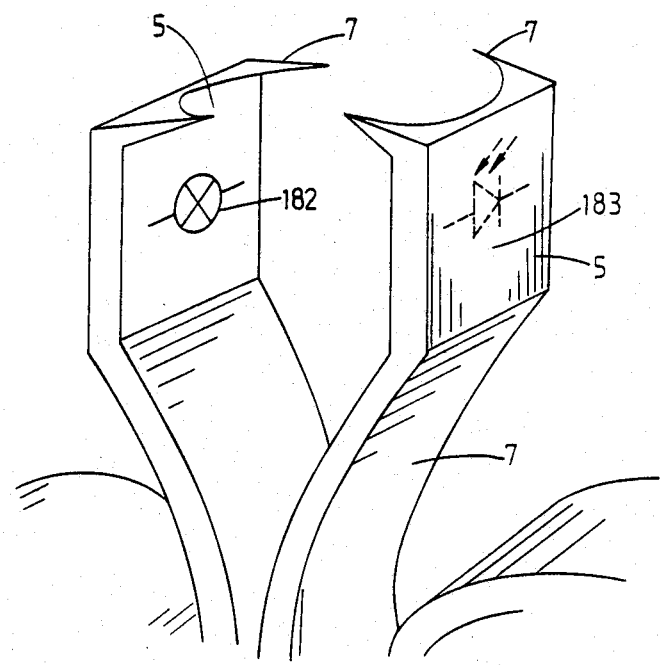
Figure 13:
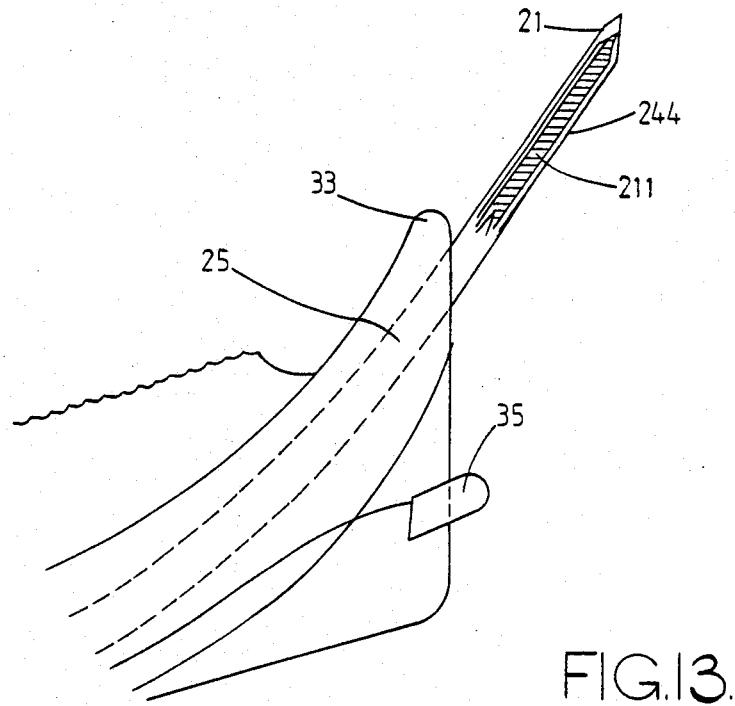
Figure 14:
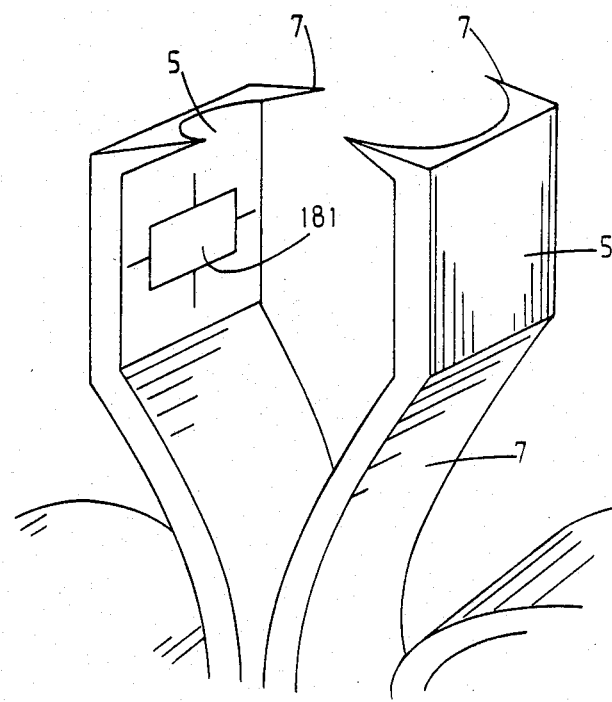

FIG. 5 are views similar to FIG. 2 of Omega-shaped test probes;

FIG. 6 and FIG. 7 are views similar to FIG. 4 of U-shaped test probes;

FIG. 8 is a schematic view showing a different embodiment of the invention comprising a probe which is constructed in the form of an expansion spring;

FIG. 9 is a schematic view showing a further modification of the probe with a screw spring;

FIG. 10 is a schematic view showing a test probe with a W-shaped spring;

FIG. 11 is an enlarged schematic illustration of part of FIG. 1 showing an alternative embodiment of a probe of the invention utilizing an NTC resistor;

FIG. 12 is an enlarged schematic illustration similar to FIG. 11 showing a further embodiment;

FIG. 13 is an enlarged schematic illustration of a part of FIG. 8 showing another embodiment of the invention;

FIG. 14 is a view similar to FIG. 13; and

Figure 15:
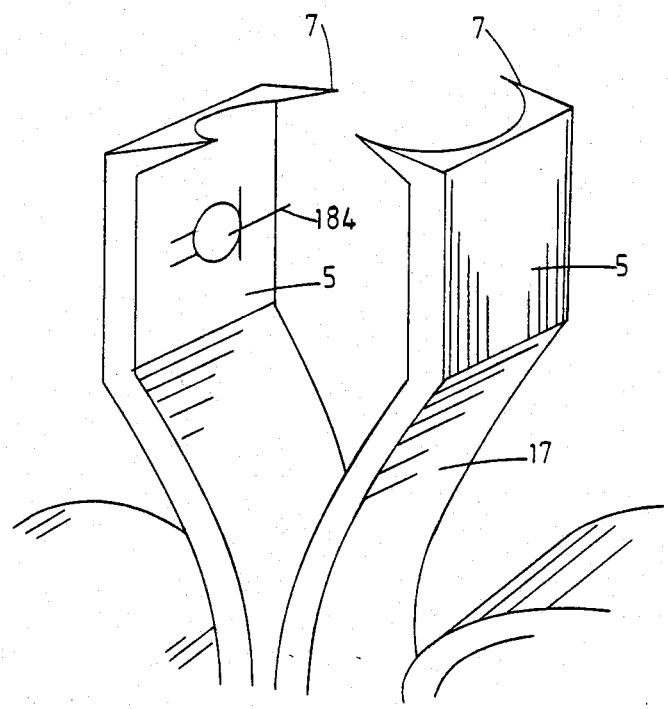

FIG. 15 is a view similar to FIG. 11 showing another embodiment of the invention.

DETAILED DESCRIPTION

The embodiments according to FIGS. 1 to 7 have in common the clip legs 1 which are associated with the spring 2 for which force-application faces 10 are provided. Furthermore all embodiments have in common the gap 3 between the clip legs 1.

It will be observed particularly clearly from FIG. 1 that the dimensions of the gap 3 are fixed in all space-coordinates. The gap width 4 depends on the state of tension of the spring. It increases when the spring is in tension in order to return to a predeterminable value on relaxation of the spring which value corresponds to the skin fold drawn in between the legs. This skin fold is drawn into gap 3 across the whole breadth 9 to a height 6. The juxtaposed faces of the clip legs 1 are then pressed directly against the skin surface in the relaxed state of the spring unless they are used, in the sense of the present invention to mount further sensors of measuring apparatus which would then engage with the skin. In FIG. 1 the left clip leg schematically shows a mounted acceleration pick-up 18. The relative distance of the teeth 7 which are provided at the extremities of the clip legs 1 is always less than the width 4 of the gap 3 so that the skin fold is effectively fixed. In the embodiments according to FIGS. 1 and 2 curved junction zones 8 are provided between the clip legs 1 and the spring 2 and their curvature is directed opposite relative to that of the spring 2. In the embodiment of FIG. 3, each leg 1 and spring 2 is connected by a junction zone which is of a bent configuration. In the embodiments according to FIGS. 1 and 2 these junction zones 8 touch one another along a line 17 which extends in the direction of the breadth 9 of gap 3. On load application to the force-application faces 10 the junction zones 8 roll off on one another along this touchline and are thus able to open or close the clip legs. In the embodiment according to FIG. 3 the junction zones 8 mutually penetrate as already described so that again the gap 3 will be closed when pressure is applied to the force application faces 10.

The embodiments shown in FIGS. 4 and 5 make use of an omega-shaped clip. Here the clip legs 1 directly adjoin the spring 2 and merge terminally into outwardly extending foot portions which are capable of transmitting the application force of forceps 19 to the spring 2. To this end the forceps 19 according to FIG. 4 are provided with forceps tips 11 which are adapted to be inserted in matching holes or recesses 14 provided in the foot portions 12. In modification of this arrangement FIG. 5 shows an embodiment in which the foot portions 13 are bent back in the direction towards the clip legs 1. This creates a space for the positive flush engagement of a blunt, headtype forceps tip 15. The drawing readily shows that the transition from the foot portions to the forceps tips can be easily designed such as to achieve a very largely rounded-off configuration.

Lastly, FIGS. 6 and 7 show a particularly simple embodiment of the invention in which the clip is of U-configuration. The curved part of the U forms the actual spring 2 with adjoining rigid clip legs 1. The latter, as shown in FIG. 7, are provided either with juxtaposed teeth 16 on their inner sides or with teeth 16 of this kind on one side only whilst the other side is provided with one or more points 7'. The clip is shown in relaxed state in FIGS. 6 and 7. By introducing the tips of forceps into the clip and applying them to the force-application faces 10 this clip can be expanded in order to be set down in this state on the skin of the foetal head.

The embodiments according to FIGS. 1 to 7 comprise conductor cables which, for the sake of simplicity, is actually represented in FIG. 2 only. The conductor cable 20 is connected to the outside of one of the two clip legs 1. Next to the probe the cable 20 extends through, but insulated from in a known manner, a bright metal cylinder 45 to which latter the further cable 20' is connected. In this way a reference potential is obtained which is in contact with the mother.

Besides these conductor means which are provided in all embodiments further sensors of further measuring devices may be provided, as already mentioned, FIG. 1 schematically representing an acceleration pick-up 18 by way of example. Instead of such a pick-up 18 there may be, in particular, electrodes for transcutaneous partial oxygen pressure measuring of the type described in the publication "Cutaneous Oxygen Monitoring in the Newborn", Paediatrician, Vol. 5, No. 5-6, 1976 page 342.

Likewise, a Hall- or accoustic resonance generator 181 may be secured to the inside of one clip leg as shown schematically in FIG. 14 by means of which it is possible to pick up movements relative to the magnetic field of the earth. Such a Hall generator is being offered under the Type designation SAS 231 L by the firm Siemens Aktiengesellschaft, Erlangen, West Germany. For a Hall-generator of this kind, which would take the place of the acceleration pick-up 18, five derivation conductors in all would be needed in order to provide the feed lines for supply voltage and the output lines for the output potential An illustration of this system in the drawings has been dispensed with in order to afford a clearer overall picture. However, they would come out on the free side of clip leg 1.

In the case of an acceleration-pick-up, on the other hand, four conductors would be sufficient. A suitable model carries the type designation EGA-125-500 and is supplied by the firm Entran International Fairfield, N.J. USA.

With the aid of just three conductors a conventional microphone 184 such as shown schematically in FIG. 15 could be fitted whereas a photo-optical device comprising a light source 182 and a photo-diode 183 as shown schematically in FIG. 12 would require four conductor lines.

The embodiment according to FIG. 8 comprises angled portions 25,26 adjoining a V-shaped spring 24 and prolonged in contact points 21,22. The angular position of these contact points 21,22 relative to the longitudinal axis 23 of the probe is such that in the compressed state of the V-spring 24 they have an inferior inclination relative to said longitudinal axis 23 than in the relaxed state of the spring. The dotted line 21' illustrates the position of spring and contact point in the tensed state of the spring In the relaxed state the contact points adopt an almost right angle position relative to the longitudinal axis 23.

The V-shaped plastic sheath or envelope 27 comprises on both sides thereof forceps-pressure faces 28,29 which may be rendered even more efficacious by grooving, corrugations or the like Thus it is possible to keep the V-spring closed by closing the forceps.

In addition to the contact points 21 from which issues a joint output cable 31, there is further provided a blunt electrode 30 in the vicinity of the tip of the plastic sheath 27 which is branched as mother electrode and from which issues the output cable 32.

The V-shaped sheath or casing 27 also encases the angled portions 25,26. At this point the sheath comprises portions 33 and 34 which are flattened out in such a way as to limit the penetration depth of the contact points 21, 22.

Each section 33,34 carries a measuring element 35, one of which is, for example, an NTC resistor. From each issues an output cable 36,37. Contact point 22 is furthermore constructed as an injection needle with an injection tube 244 attached thereto, as shown schematically in FIG. 13. Optionally it could also accommodate the NTC resistor 135 with its output cable as shown in FIG. 11.

In the embodiment according to FIG. 9 like parts carry like references as in FIG. 1. However, here the plastic sheath 27 is not V-shaped but approximately circular in cross section. Inside the sheath an output cable 31,31' for each of the two contact points 21,22 is supported in insulated manner. Moreover, the sheath also houses the two insulated cables 32,32' of the reference potential which issue from the blunt electrodes 30,30'. Inside the plastic sheath 27 there is provided an integral plastic cylinder 40 extending in the longitudinal direction of the probe and accommodating a coiled compression spring 39. The leading edge of the cylinder has an annular shoulder 41 which in the illustrated position is engaged by the opposite shoulder of the housing for a further measuring element 42. In this position the further measuring element 42 is maintained by the relaxed coiled spring 39 in the free space 43.

Thus the test probe according to FIG. 9 is likewise in the application state. For the preceding stage of introduction the measuring element 42 was pushed back into space 43 thus compressing the spring 39 whilst the plastic sheath 27 was kept or held closed by means of forceps applied to the forceps pressure faces 28 and 29. The load-relieving of these faces 28,29 thereupon caused the measuring element 42 to be pushed forward and at the same time caused the spreading out of contact points 21,22.

In other words, the further measuring element 42 is subject to the influence of the spring 39 while it is in function.

This arrangement assures particularly effective skin contact. It will be understood that such a further measuring element need not necessarily be just a microphone but could also be, for example, an acceleration pick-up or a sensor for the determination of space coordinates, or a sensor for reflexion and transmission-measurements. Transmission is possible when the contact points 21,22 are directly opposite one another beneath the skin. Such measurements are of great interest for continuous monitoring because they allow valuable conclusions to be drawn concerning the blood circulation and thus acute changes in the circulatory situation such as for example centralization phenomena. Light sources and photo-receivers for this purpose can be mounted in the region of the contact points.

As already mentioned, at least one of the contact points may be a hollow injection needle as shown in FIG. 13. Not only does this enable the connection of a tube or hoseline but such an injection needle may also be used to introduce a pH measuring electrode. Such a measuring electrode 211 is known from the publication "Innovation in Instrumentation" by the firm World Precision Instruments, Inc. New Haven Conn. USA, where it is more specifically called a Beetrode. Such a pH-measuring electrode can be very well guided and secured against breaking off inside a contact point of the hollow needle type.

FIG. 10 shows an arrangement in which the contact points 21 and 22 are provided at the extremities of a substantially W-shaped spring. This figure represents the state of tension. In the relaxed state the contact points 21,22 are spread apart and assume a fixed position in the skin of the foetal head which is pretermined by the relaxation state of the spring. In this state the inner section 44 of the spring is pressed in the direction towards the skin of the foetal head and presses the measuring element 42 against this skin.

I claim:

1. A physiological test probe for transcervical attachment to the headskin of a foetus and provided with a signal cable, said probe comprising: a pair of legs each of which is formed as a flat strip extending in a straight direction and having mutually opposing parallel surfaces; a spring bent into the shape of a partially circular ring connected to said legs so that the legs and spring together form a clip; a junction zone between each leg and the spring, each junction zone being bent with a curvature which is opposite to the curvature of the spring, said junction zones touching each other along a line extending in the direction of the breadth of the gap between the legs in any state of the spring; and inwardly directed punctiform teeth provided on said legs and spaced apart by a distance which is less than the distance between said legs; an open position of said legs corresponding to a stressed state of said spring so that said legs move towards each other from the open position when the spring is relaxed and, in use, as the spring is relaxed from its stressed state, a fold of headskin is drawn between said mutually opposed surfaces, said mutually opposed surfaces defining the length and breadth of said fold of skin and the relative distance between said mutually opposed surfaces assuming a predetermined value.

2. A physiological test probe as claimed in claim 1 wherein each clip leg is provided with a force application area.

3. A physiological test probe as claimed in claim 1 and further comprising at least one sensor mounted on the inner surface of one of said legs.

4. A physiological test probe for transcervical attachment to the headskin of a foetus and provided with a signal cable, said probe comprising: a pair of elastic and invasive contact points; a spring connected to said pair of contact points so that the contact points are inclined obliquely forwardly with respect to the longitudinal axis of the probe; plastic sheathing mounted on said spring and providing at least one depth defining end stop, so that, in use, as the stress in the spring is varied between a stressed state and a relaxed state, the spacing between the contact points varies and the contact points remain in a jointly defined common plane, the spacing between the contact points when the spring is in a relaxed state being determined by the spring, and the depth to which the contact points penetrate the headskin being limited by said at least one depth defining end stop; a measuring element movably mounted in the space between the contact points; a second spring biasing said measuring element for movement forwardly along the longitudinal axis of the probe; and means for permitting such forward movement when the stress in the first spring is relaxed from a stressed state, so that, in use, said measuring element is applied to the foetal headskin.

5. A physiological test probe as claimed in claim 4 wherein said spring includes a pair of angled end portions each of which is integral with a respective one of said contact points.

6. A physiological test probe as claimed in claim 4 wherein the probe is provided with a second signal cable terminating at a position spaced from said contact points and providing a reference potential.

7. A physiological test probe as claimed in claim 4 and further comprising an individual conductor cable connected to each of said contact points.

* * * * *